US006874506B2

(12) United States Patent
Chapman

(10) Patent No.: US 6,874,506 B2
(45) Date of Patent: Apr. 5, 2005

(54) RAPID DEPLOYMENT SEAT-BASED RELEASABLE SOFT RESTRAINT SYSTEM AND METHOD

(75) Inventor: Bruce Chapman, Gardiner, NY (US)

(73) Assignee: HWC, Inc., Gardiner, NY (US)

( * ) Notice: Subject to any disclaimer, the term of this patent is extended or adjusted under 35 U.S.C. 154(b) by 368 days.

(21) Appl. No.: 10/044,715

(22) Filed: Jan. 11, 2002

(65) Prior Publication Data

US 2002/0092528 A1 Jul. 18, 2002

Related U.S. Application Data

(60) Provisional application No. 60/261,327, filed on Jan. 13, 2001.

(51) Int. Cl.$^{7}$ .................................................. A61B 19/00

(52) U.S. Cl. ........................ 128/869; 128/878; 119/770; 119/771; 297/464; 297/466; 297/468; 297/485

(58) Field of Search ................................ 128/869, 870, 128/878, 879; 119/770, 771; 297/464, 466, 468, 469, 473, 474, 476, 482, 485

(56) References Cited

U.S. PATENT DOCUMENTS 4,173,974 A * 11/1979 Belliveau ....................... 70/16
4,813,745 A * 3/1989 Woody ........................ 297/464
4,930,842 A * 6/1990 Wilkinson et al. .......... 297/466
5,106,121 A * 4/1992 Boone ......................... 280/807
5,499,844 A * 3/1996 Dirck .......................... 280/748
5,758,892 A * 6/1998 Hogan ...................... 280/250.1
6,360,747 B1 * 3/2002 Velarde et al. .............. 128/869

* cited by examiner

*Primary Examiner*—Henry Bennett
*Assistant Examiner*—Camtu Nguyen
(74) *Attorney, Agent, or Firm*—Edward Etkin, Esq.

(57) ABSTRACT

An apparatus and method for rapidly restraining a person for an extended period of time at a seat are disclosed. The inventive apparatus includes a pair of wrist cuff modules, each supplied with a releasable connector, configured to either attach to existing hardware on one or more seats, or to a first interconnect for releasably connecting the wrist cuff modules to one another behind the seat in which the restrained person is positioned. A set of two ankle cuff modules with a second interconnect and an elongated connection member secured to the second interconnect is provided for securing the person's legs by applying the ankle cuff modules to the ankles and then connecting the connection member to a seat. The second interconnect may be provided with an optional quick release mechanism that enables instant disconnection of the second interconnect from the ankle cuff modules to immediately free the person's legs in case of an emergency.

29 Claims, 5 Drawing Sheets

RAPID DEPLOYMENT SEAT-BASED RELEASABLE SOFT RESTRAINT SYSTEM AND METHOD

REFERENCE TO PREVIOUSLY FILED APPLICATIONS

The present patent application is a continuation-in-part of a previously filed commonly assigned U.S. Provisional Patent Application Ser. No.: 60/261,327, entitled "Rapid Deployment Releasable Airplane Passenger Soft Restraint System and Method" filed on Jan. 13, 2001.

BACKGROUND OF THE INVENTION

The present invention is directed to a soft mechanical restraint system that may be easily and quickly deployed by a first person on a subject being held in a restrained position by a second person, and then attached to one or more seats, such that the subject is safely restrained for an extended period of time in relative comfort.

There are many thousands of human service and law enforcement agencies and facilities that provide care and supervision to aggressive, suicidal, and emotionally disturbed persons or otherwise dangerous persons (hereinafter commonly referred to as "EDPs").

Another common problem faced each day by airline and other transportation personnel (e.g. train conductors, bus drivers, etc.) is dealing with intoxicated or aggressive passengers. For example, "air rage" is a serious problem that poses a great danger to airline safety. Emotionally disturbed and/or intoxicated passengers may get out of control and threaten the safety of other passengers and airline crew members as well as their own safety. Furthermore, potential hijackers and other dangerous persons may also pose a significant threat to airline safety.

During "air rage", hijack attempts, or other vehicle-related incidents, the dangerous and/or aggressive passengers may need to be restrained by untrained individuals such as other passengers and crew members, and then held down for extended periods of time. In one recent incident, an aggressive airline passenger restrained by fellow passengers died due to positional asphyxiation from an improperly applied hold. While this is less of an issue in a hijack situation, such incidents point to the fact that restraint of dangerous persons on an airplane or other public vehicle (such as a train or a bus) poses a danger not only to other passengers and vehicle personnel, but also to the restrained individuals themselves.

In addition, staff and officers working in human service and law enforcement agencies and facilities that provide care and supervision to aggressive, suicidal, and emotionally disturbed persons, regularly come into physical contact with the EDPs through the use of physical subduing or restraint holds when the EDP becomes aggressive.

Although there are many types of well-known physical subduing holds, the safest and most advantageous physical subduing hold is a Primary Restraint Technique (PRT) described in greater detail in a commonly assigned U.S. Pat. No. 6,273,091 entitled "APPARATUS AND METHOD FOR SAFELY MAINTAINING A RESTRAINING HOLD ON A PERSON". The PRT approach is particularly advantageous in confined areas such as vehicle (e.g. airplane, train, or bus) aisles.

While restraint holds, such as the PRT, are useful for relatively short periods of time, often restraint of the EDP is necessary for an extended period. This is especially true when the EDP must be restrained in a vehicle, or is otherwise being transported in a vehicle. In such cases, the EDP must be restrained using some sort of a mechanical restraint system. Typically, this involves placing wrist and ankle mechanical restraints on the EDP so that the EDP may be restrained for an extended period of time at or near the place of the restraint hold, or transported to another location while wearing the restraints. Most previously known restraint systems involve mechanical locks—for example, one popular restraint utilizes a mechanical spring-loaded lock that requires a special key to open. It takes at least 4–5 staff members to successfully apply such restraints at a speed of no lower than 2–3 minutes per restraint. During the application of these restraints, the EDP must be held down and poses a constant threat to the staff members until the restraining process is complete. Such a concerted effort is simply impossible aboard most vehicles because of the limited space available. For example, no more than two persons in addition to the EDP may operate in an airplane aisle.

Furthermore, removal of such restraints in emergency situations (i.e. in a medical or other emergency) takes a significant amount of time since a key must be located and used to open each restraint on each limb—this is especially problematic because without the key, which may not be immediately available in case of an emergency, the restraints cannot be removed at all. This is particularly dangerous when the EDP is being restrained in a vehicle because if the vehicle suffers an accident, the EDP may need to be removed from the vehicle very quickly. Moreover, even after the EDP is placed in a previously known restraint system, there is no way to place the EDP in a comfortable restrained position where the EDP will not pose a danger to themselves or to others, unless the EDP is subjected to constant supervision and observation. Finally, such complex restraint systems are expensive, heavy, and require extensive training to use properly.

Manipulation of the previously known restraints once attached is difficult as well, requiring several people to pull webbing through complex system of buckles and connectors to connect cuff restraints to one another. And often, once an EDP is moved to a stationary restraint area, such as a seat, the restraints used during EDP transport must be removed and replaced with stationary restraints.

Some of the above problems and challenges are advantageously solved by a novel circular cuff module that may be applied to each of an EDP's limbs quickly (and removed therefrom) by staff members without use of complex locking mechanisms that is disclosed in the commonly assigned co-pending U.S. patent application entitled "Soft Circular Restraint Apparatus and Method" incorporated herein by reference in its entirety. Several advantageous approaches to interconnecting the novel cuff modules are disclosed as well.

However, one of the main challenges of previously known restraint systems, including the one disclosed in the above-incorporated "Soft Circular Restraint Apparatus and Method" patent application, is in how the cuff restraints are connected to stationary positions such as vehicle or other seats where the EDP may be secured for an extended period of time. This issue is of particular importance when the EDP is restrained aboard a vehicle. Of course custom designed seats with built-in stationary restraints may be provided, but such an approach is very expensive and significantly limited in usefulness.

Another issue is how the wrist and ankle restraints are connected to one another. While connecting ankle cuff modules to one another by a simple interconnect may serve to prevent the EDP from kicking, application of a simple wrist interconnect may pose a problem with particularly violent and/or aggressive EDPs. Similarly, while a simple wrist interconnect may prevent the EDP from using their hands independently from one another, the EDP is not prevented from flailing their arms at elbows and shoulder if the restrained wrists are at the EDP's front, where the EDP may still attack other persons even if the wrists are pulled together. Securing the EDP's wrists behind their back is a partial solution, but a nimble EDP can contort themselves to move their wrists to the front of their body. With respect to ankle restraints, while the novel circular cuff modules, disclosed in the above-incorporated patent application, include connectors to releasably connect to stationary connectors (such as may be disposed on a bed), other types of ankle modules and respective interconnects do not possess any mechanism to connect to stationary connectors. Most importantly, most previously known restraint systems cannot be releasably but securely connected to stationary areas, such as ordinary vehicle seats, and, even if securely connected to such areas, cannot be quickly released in case of an emergency.

Thus, it would be desirable to provide an apparatus and method for quickly and easily applying mechanical restraints to a person being controlled through a restraining hold, or who is otherwise immobile, in a confined area such as a vehicle aisle. It would furthermore be desirable to provide a mechanical restraint apparatus that is relatively comfortable to the subject and that may be quickly and easily removed in case of an emergency. It would additionally be desirable to provide a mechanical restraint system that severely restricts the range of motion of the person's arms and legs. It would further be desirable to provide a mechanical restraint system that can be attached to commonly used vehicle or other seats. It would also be desirable to provide a lightweight mechanical restraint system that is easy to transport and use and that is inexpensive to manufacture. Moreover, it would be desirable to provide a mechanical restraint system that may be easily be placed in an extended restraint mode without requiring additional equipment.

SUMMARY OF THE INVENTION

The apparatus of the present invention, and method of use thereof, remedies the problems associated with applying mechanical restraints to violent and/or struggling EDPs (and with removing the restraints therefrom). In brief summary, the inventive rapid deployment restraint apparatus advantageously provides: (1) quick and easy application to the EDP in a confined area such as a vehicle aisle, as well as quick and easy removal in case of an emergency; (2) severe restriction to the range of motion of the EDPs arms and legs; (3) easy attachment to commonly used vehicle or other seats; (4) lightweight and simple construction making the inventive restraints easy to transport and use and inexpensive to manufacture; and (5) easy placement in an extended restraint mode without requiring additional equipment.

The inventive apparatus and method enables rapid restraint of the EDP for an extended period of time at a seat and also enables quick release of the EDP in case of an emergency. The inventive apparatus includes a pair of wrist cuff modules each supplied with a releasable connector configured to either attach to existing hardware on one or more seats, or to a first interconnect for releasably connecting the wrist cuff modules to one another behind the seat in which the EDP is positioned. A set of two ankle cuff modules with a second interconnect and an elongated connection member secured to the second interconnect is provided for securing the EDP's legs by applying the ankle cuff modules to the ankles and then connecting the connection member to a seat. The second interconnect may be provided with an optional quick release mechanism that enables instant disconnection of the second interconnect from the ankle cuff modules to immediately free the EDP's legs in case of an emergency.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote corresponding or similar elements throughout the various figures.

DESCRIPTION OF THE PREFERRED EMBODIMENTS

Figure 1A:
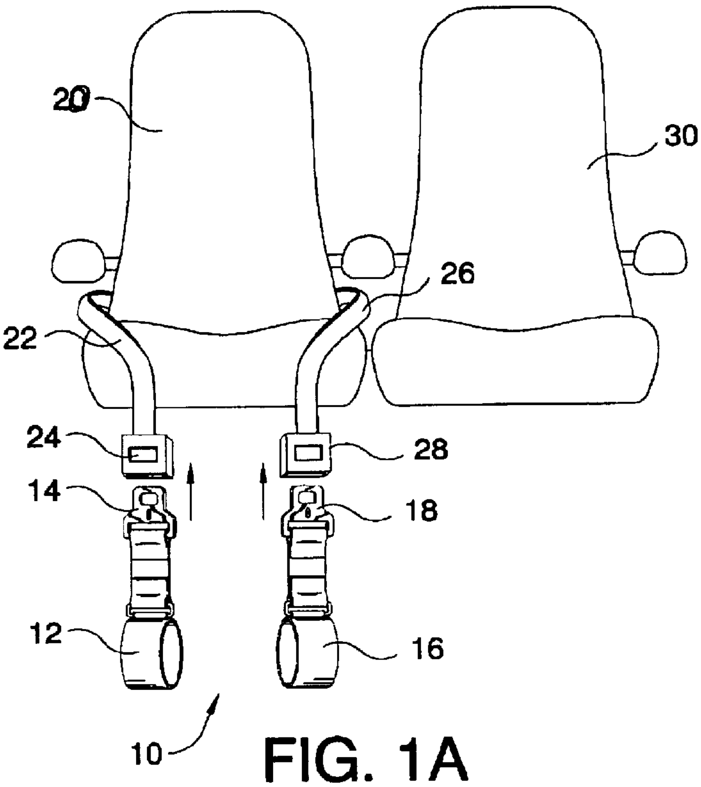
FIG. 1A is a front/top view of a first embodiment of an arm restraint apparatus of the present invention deployed on a seat.

The present invention relates to an advantageous soft mechanical restraint apparatus and method that may be quickly and easily applied by a first person to a subject being held in a restraining hold by a second person in a confined area, and that may be secured to common vehicle or other seats to restraint the subject for an extended period of time in relative comfort.

It should be understood that while the present invention refers to EDPs, the inventive apparatus, and methods of use thereof, may be applied in virtually any situation where a subject is being restrained and application of mechanical restraints is warranted. Furthermore, while the present invention is described with regard to vehicle seats, it may be advantageously utilized with seats of any other type. Moreover, the various embodiments of the present invention are described with reference to male and female seat-belt type connectors by way of example only. It should be understood to one skilled in the art that other matched releasable connector sets may be readily substituted for seat-belt type connectors without departing from the spirit of the invention. Finally, the male and female seat-belt type connectors shown in the figures and described as mounted on various elements of the inventive apparatus, may be readily interchanged with one another without departing from the spirit of the invention.

Before application of any sort of mechanical restraints, it is important that control over a struggling EDP is established by placing the EDP into a restraining hold. The Primary Restraint Technique (hereinafter "PRT") is an advantageous modular single person restraint that is applied by an EDP care professional (hereinafter "staff member") to an EDP from behind. The maneuvers involved in implementing the PRT are described in greater detail in Primary Restraint Technique (PRT) described in greater detail in a commonly assigned U.S. Pat. No. 6,273,091 entitled "APPARATUS AND METHOD FOR SAFELY MAINTAINING A RESTRAINING HOLD ON A PERSON" which is hereby incorporated by reference in its entirety. It should be noted, however, that the restraint apparatus of the present invention does not require use of the PRT—it may be advantageously be utilized in any situation where the EDP is physically restrained by one or more staff members or other individuals. Of course, if the EDP is not ambulatory (i.e. unconscious or asleep), it is not necessary to apply any restraint holds before application of the inventive restraints. The PRT is particularly advantageous for deployment of the inventive apparatus in a vehicle aisle because the PRT works well in confined areas and only requires a single person to restrain the EDP while the inventive apparatus is being applied.

In summary, the seat-based restraint apparatus of the present invention comprises: (1) an arm restraint system with a wrist cuff module for each wrist, each wrist cuff module supplied with a releasable connector for securing the wrist cuff module to available corresponding releasable seat connectors positioned either on the seat in which the EDP is positioned or on one or more proximal seats. If releasable seat connectors are not available, a flexible first interconnect is supplied for releasably connecting the wrist cuff modules to one another behind the EDP's seat; and (2) a leg restraint system with an ankle cuff module for each ankle, a flexible second interconnect for connecting the ankle cuff modules to one another, and a connection element positioned on the second interconnect and supplied with a releasable connector, that can be used to substantially immobilize the EDPs legs by securing them to the seat in which the EDP is restrained, or to another proximal seat. The leg restraint system may be provided with an optional quick release mechanism for instantly releasing the leg restraint system in case of an emergency.

It should be understood to one skilled in the art that the arm and leg restraint systems of the present invention can be readily utilized independently from one another without departing from the spirit of the invention. For example, in certain situations only the arm restraint system may be used, while in another situation, only the leg restraint system may be utilized.

Referring now to FIG. 1A, an arm restraint system 10 is shown. The arm restraint system 10, includes a first wrist cuff module 12 having a releasable connector 14 attached thereto, and a second wrist cuff module 16 having a releasable connector 18 attached thereto. The releasable connectors 14, 18 are preferably elongated flexible members (for example, composed of nylon or other webbing) terminating in male seat belt connectors (although as noted above, female seat-belt connectors may be readily substituted).

Preferably, the cuff modules 12 and 16 are the circular cuff modules described in the co-pending commonly assigned U.S. patent application entitled "Soft Circular Restraint Apparatus and Method", which is hereby incorporated by reference in its entirety. One of the advantages of the circular cuff modules is that they possess integrated the releasable connectors (e.g. releasable connectors 14, 16), and are quick and easy to apply to the EDP.

However, the arm restraint system 10 may be utilized with a set of any other generally circular cuff modules (for example, any commercially available resilient cuff restraints) as long as each cuff module includes (or is modified to include) the releasable connectors 14, 18. It should be noted that the cuff modules 12, 16 are shown in simplified views in the various figures and may include additional elements (such as locking mechanisms) that are not shown in the figures because such additional elements are not relevant to the present invention.

Most vehicle seats (such as car, airplane or bus seats) shown as seats 20, 30, include existing seat-belt type hardware, such as a flexible member 22 with a releasable connector 24 and a flexible member 26 with a releasable connector 28, either on or between the seats, that are used for securing seat-belts around passengers. Optionally, any vehicle or non-vehicle seat 20 may be modified to include securely fastened flexible members 22, 26 with respective releasable connectors 24, 28.

Figure 1B:
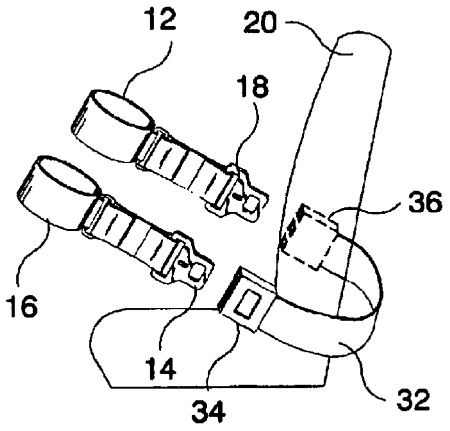
FIG. 1B is a side/partially isometric view of a second embodiment of the inventive arm restraint apparatus being deployed on the seat.
Figure 1C:
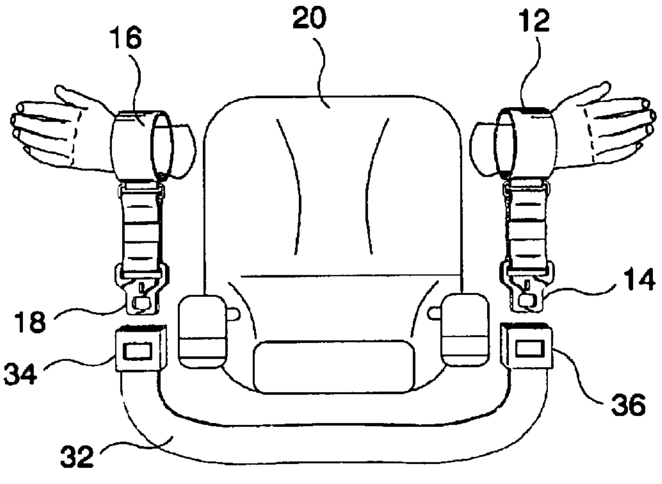
FIG. 1C is a top view of the arm restraint apparatus of FIG. 1B deployed on the seat.
Figure 1D:
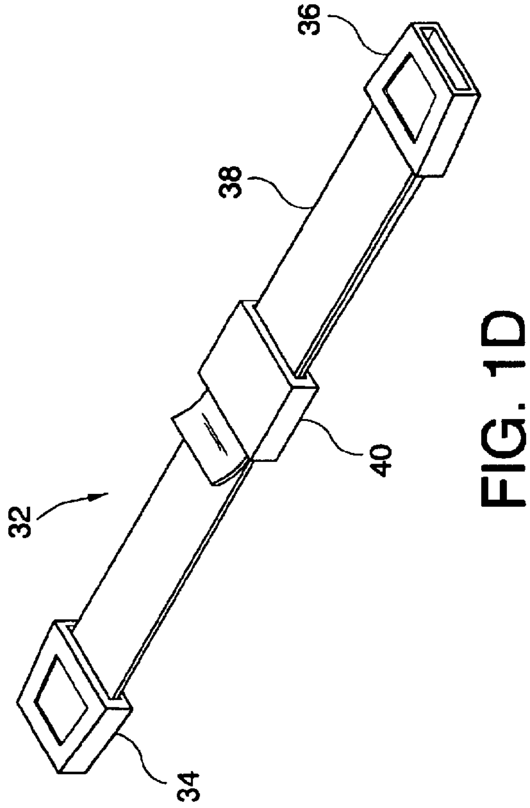
FIG. 1D is a top isometric view of an arm restraint interconnect used in conjunction with the arm restraint apparatus of FIG. 1B.

Referring now to FIGS. 1B to 1D, when flexible members 22, 26 with respective releasable connectors 24, 28 are not available (for example, not supplied with the seat 20, or used for seat-belts of other nearby persons), a flexible wrist interconnect 32 may be provided. The interconnect 32 includes an elongated body 38 composed of a strong flexible material such as nylon webbing (for example, such as webbing used in seat belts and parachute straps) with a first end having a releasable connector 34 mounted thereon, and a second end having a releasable connector 36 mounted thereon. The releasable connectors 34, 36 are preferably configured to releasably connect to respective releasable connectors 14, 18. Thus, the releasable connectors 34, 36 are preferably female seat-belt type connectors (or male seat-belt type connectors if the releasable connectors 14, 18 are configured with female seat-belt type connectors). The interconnect 32 is placed behind the seat 20 (in which the EDP is restrained) and connected to the releasable connectors 14, 18, thereby restricting the motion of the EDP's arms.

The interconnect 32 may be supplied with an optional tensioning device 40, such as a tensioning buckle passing a portion of the interconnect body 38 therethrough, for controlling the length of the interconnect 32. Thus, when the interconnect 32 is connected to the releasable connectors 14, 18, the tensioning device 40 may be activated to tighten the interconnect 32 to advantageously further restrict the motion of the EDP's arms.

Optionally, the EDP's arms may be further immobilized by securing the EDP's wrists to the sides of the EDP's body by utilizing an additional wrist cuff module interconnect (not shown) that releasably connects to the cuff modules 12, 16 and around the EDPs body, and serves to further secure the EDP in the seat 20. Preferably, the additional wrist cuff interconnect is one disclosed in a commonly assigned co-pending U.S. patent application entitled "Rapid Deployment Soft Restraint Apparatus and Method" which is hereby incorporated by reference in its entirety.

Figure 2A:
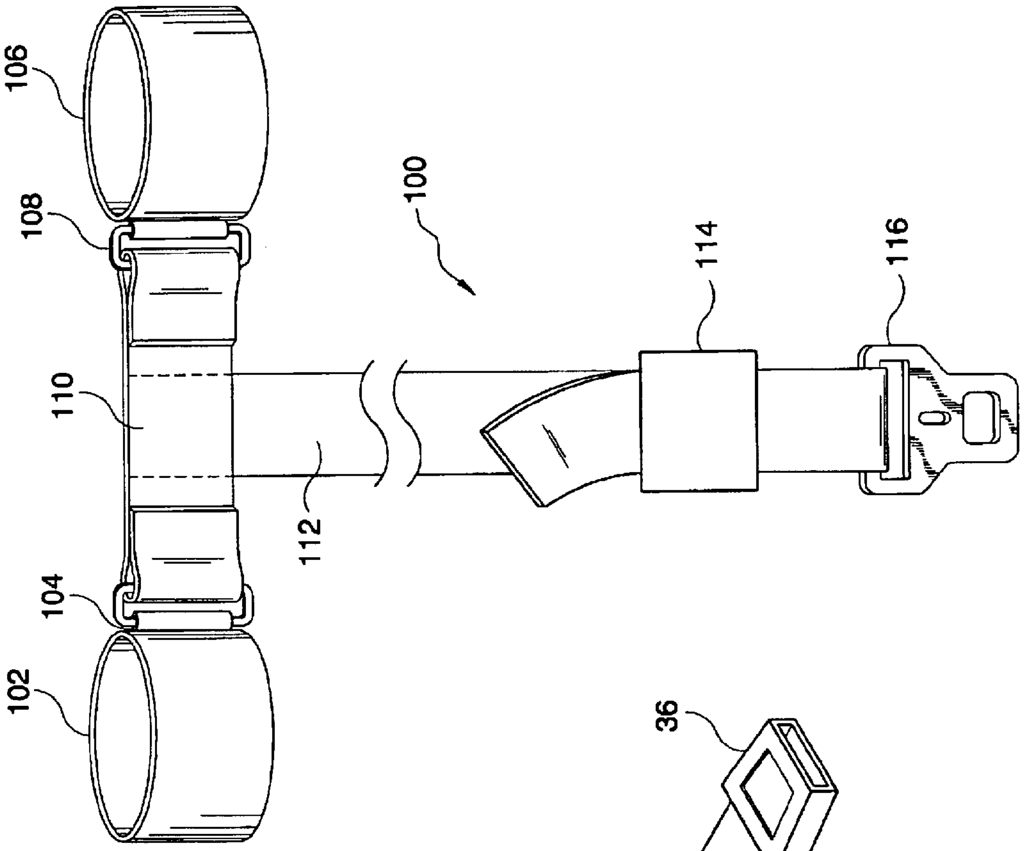
FIG. 2A is a top isometric view of a first embodiment of the leg restraint apparatus of the present invention.

Referring now to FIG. 2A, a first embodiment of the leg restraint system 100 of the present invention is shown. The leg restraint system 100 includes a first ankle cuff module 102, a second ankle cuff module 106, and an ankle interconnect 110 therebetween. The ankle interconnect 110 may be a length of flat flexible webbing (for example composed of nylon or similar material). Preferably, the cuff modules 102 and 106 are the circular cuff modules described in the co-pending commonly assigned U.S. patent application entitled "Soft Circular Restraint Apparatus and Method", which is hereby incorporated by reference in its entirety. However, the leg restraint system 100 may be utilized with a set of any other generally circular cuff modules (for example, any commercially available resilient cuff restraints) capable of connecting to an interconnect device. It should be noted that the cuff modules 102, 106 are shown in a simplified view and may include additional elements (such as locking mechanisms) that are not shown because such additional elements are not relevant to the present invention.

The interconnect 110 has its first end connected to a rigid loop 104 disposed on an outer surface of the cuff module 102 and its second end connected to a rigid loop 108 disposed on an outer surface of the cuff module 106. Optionally, the interconnect 110 may be attached to the cuff modules 102, 106 in another manner. The length of the interconnect 110 may be selected as a matter of design choice. For example, if it is very short, the EDP will be unable to walk when being transported to or from the seat 20, while if it is long, the range of motion of EDP's legs will not be sufficiently restricted.

Figure 2B:
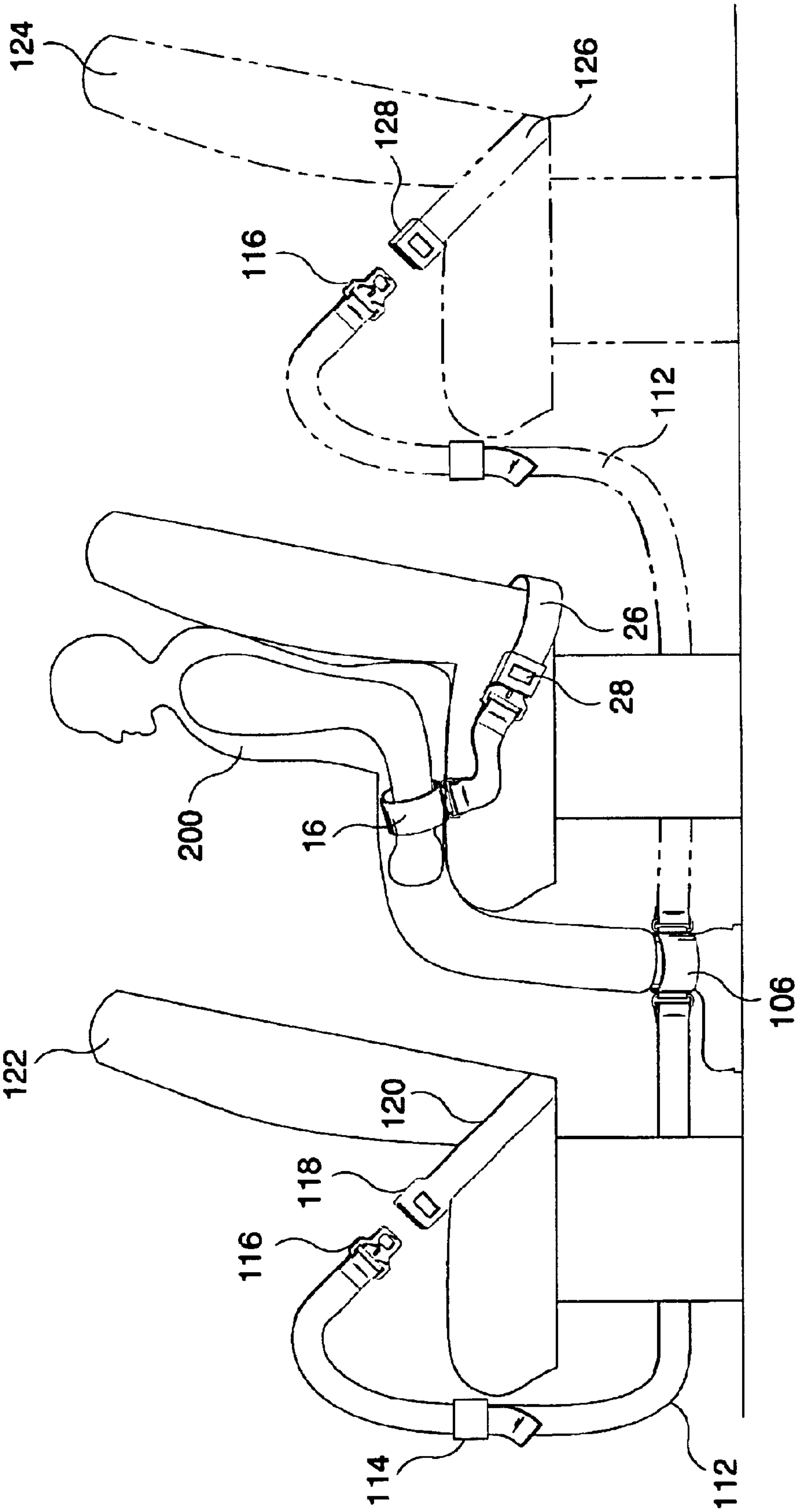
FIG. 2B is a side view schematic diagram of the arm restraint apparatus of FIG. 1B, and the inventive leg restraint apparatus of FIG. 2A deployed in an extended duration restraint mode across two seats.

An elongated connection member 112, such as flat flexible webbing (composed of nylon or similar material), is connected perpendicular to the interconnect 110, and preferably at a substantially central position of the interconnect 110. The connection member 112 is preferably of a length sufficient to secure it to a bottom portion of the seat 20 or, as shown in FIG. 2B, to another seat in front or behind the seat 20. The connection member 112 terminates in a releasable connector 116 that may be a male seat-belt type connector or a female seat-belt type connector (not shown). The connection member 112 is optionally provided with a tensioning mechanism 114, disposed thereon, for controlling the length of the connection member 112, such that when the connection member 112 is secured to a seat, the tensioning mechanism 114 may be engaged to further immobilize the EDP's legs.

Referring now to FIG. 2B, exemplary implementations of the arm restraint system 10 and the leg restraint system 100 are shown. An EDP 200 is seated in the seat 20, with the EDP's arms restrained by the cuff modules 12, 16 with the releasable connectors 14, 18 secured to respective releasable connectors 24, 28 of the seat 20. The EDP's legs are restrained by the cuff modules 102, 106 secured by connecting the connection member 112, via the releasable connector 116, to a releasable connector 118 mounted on a flexible member 120 fastened to a seat 122 in front of the seat 20, or, optionally connecting the connection member 112, via the releasable connector 116, to a releasable connector 128 mounted on a flexible member 126 fastened to a seat 124 behind the seat 20. Alternatively, the connection member 112 may be secured to another portion of one of the seats 20, 122 and 124, for example by simply wrapping it around the seat portion (not shown). In any case, the tensioning mechanism 114 may be engaged to further immobilize the EDP's legs.

Figure 3A:
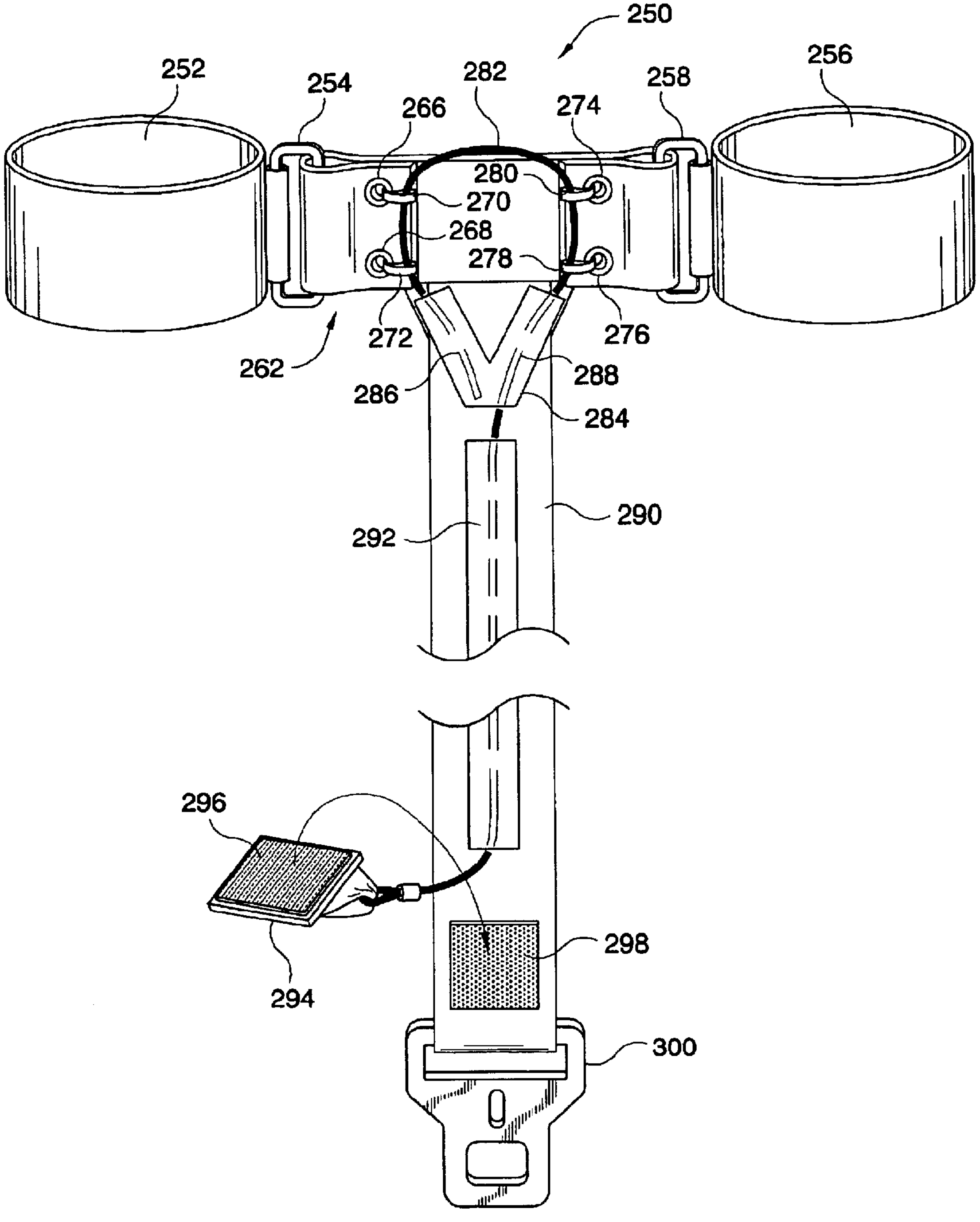
FIG. 3A is a top isometric view of a second embodiment of the leg restraint apparatus of the present invention in a closed position.
Figure 3B:
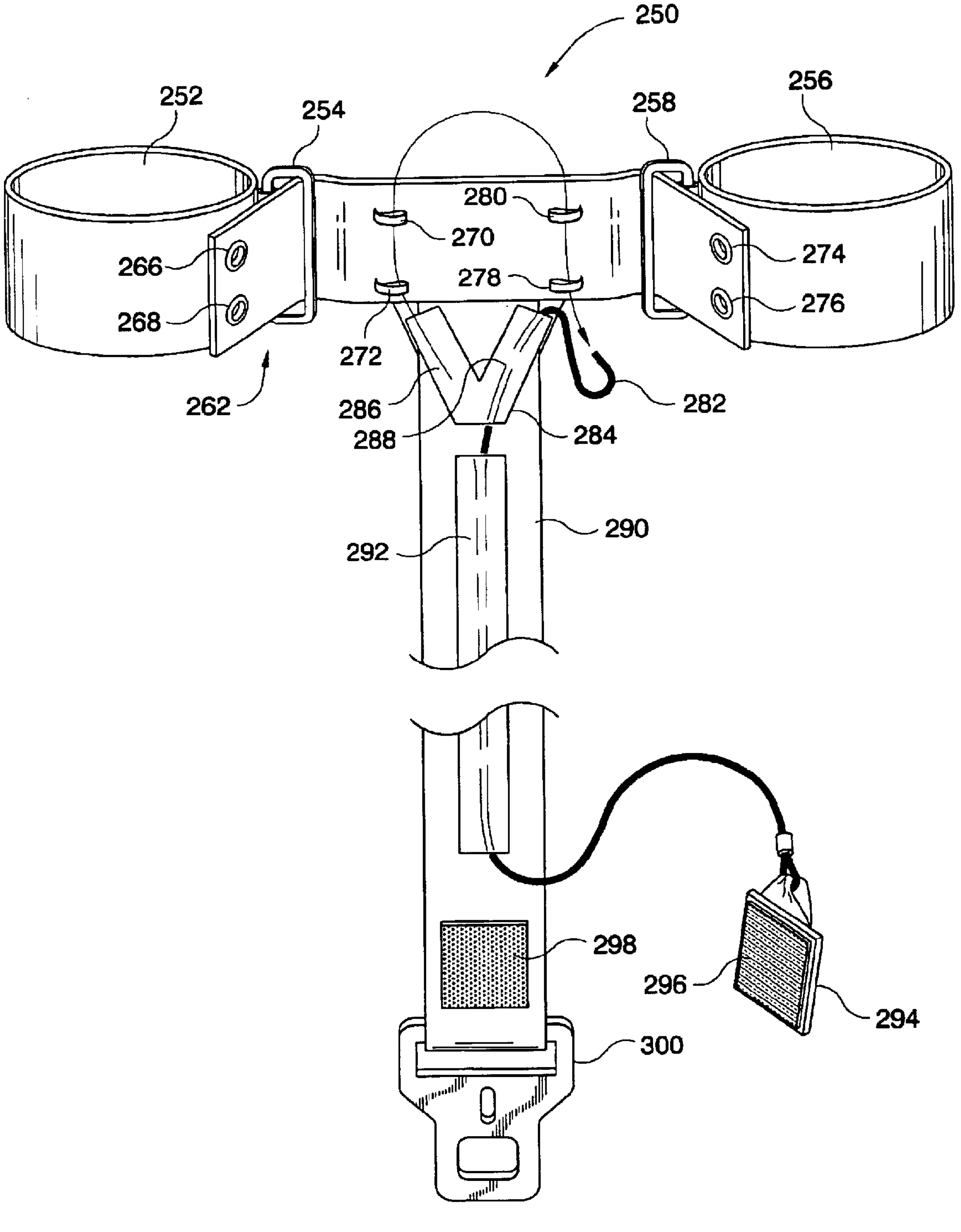
FIG. 3B is a top isometric view of the leg restraint apparatus of FIG. 3A in an open position where the leg cuff modules are released therefrom.

While the leg restraint system 100 can be released relatively quickly by disengaging the connection member 112 from the seat to which it is connected, in certain cases, such as in a vehicle emergency, or in a medical emergency, the EDP must be released from the leg restraint system 100 immediately. Referring now to FIGS. 3A and 3B, a second embodiment of the leg restraint system 100 is shown as a leg restraint system 250. The leg restraint system 250 is substantially similar to the leg restraint system 100 in construction and operation, and is utilized in a similar manner (for example, as shown in FIG. 2B), except that the leg restraint system 250 includes a quick release mechanism that enables the EDP's legs to be instantly freed from the leg restraint system 250.

The leg restraint system 250 includes a first ankle cuff module 252 having a first rigid loop 254 disposed perpendicular to its outer surface, a second ankle cuff module 256 having a second rigid loop 256 disposed perpendicular to its outer surface, and an ankle interconnect 262 releasably connected therebetween. Preferably, the cuff modules 252 and 256 are the circular cuff modules described in the co-pending commonly assigned U.S. patent application entitled "Soft Circular Restraint Apparatus and Method", which is hereby incorporated by reference in its entirety. However, the leg restraint system 250 may be utilized with a set of any other generally circular cuff modules (for example, any commercially available resilient cuff restraints) each having at least one substantially perpendicular rigid loop. It should be noted that the cuff modules 252, 256 are shown in a simplified view and may include additional elements (such as locking mechanisms) that are not shown because such additional elements are not relevant to the present invention.

The ankle interconnect 262 has a first end and a second end and may be a length of flat flexible webbing (for example, composed of nylon or similar material). The length of the interconnect 262 may be selected as a matter of design choice. For example, if it is very short, the EDP will be unable to walk when being transported to or from the seat 20, while if it is long, the range of motion of EDP's legs will not be sufficiently restricted.

An elongated connection member 290, such as flat flexible webbing (composed of nylon or similar material), and having a proximal end and a distal end, is connected by its proximal end perpendicularly to the interconnect 262, and preferably at a substantially central position of the interconnect 262. The connection member 290 is preferably of a length sufficient to secure it to a bottom portion of the seat 20 or, as shown in FIG. 2B, to a seat in front of or behind the seat 20. The connection member 290 distal end terminates in a releasable connector 300 that may be a male seat-belt type connector or a female seat-belt type connector (not shown).

The interconnect 262 includes a first elongated loop 270 positioned perpendicular to its top surface at a predetermined distance from its first end, and a second elongated loop 272, positioned next to the elongated loop 270, also perpendicular to its top surface at the same predetermined distance away from its first end. The elongated loops 270, 272 may be composed of wire, plastic or an elastic material. The interconnect 262 also includes a first hole 266 defined proximal to its first end, and a second hole 268, next to the hole 266, also defined proximal to its first end, the holes 266, 268 being positioned and sized such that when the first end of the interconnect 262 is threaded through the rigid loop 254 from bottom to top and then folded upon itself, the holes 266, 268 are aligned with the respective elongated loops 270, 272 so that the elongated loops 270, 272 pass through the respective holes 266, 268 to thereby at least temporarily connect the first end of the interconnect 262 to the rigid loop 254. The holes 266, 268 may optionally be reinforced with rings (for example made from metal or plastic) as shown in FIGS. 3A–3B.

The interconnect 262 also includes a third elongated loop 278 positioned perpendicular to its top surface at a predetermined distance from its second end, and a fourth elongated loop 280, positioned next to the elongated loop 278, also perpendicular to its top surface at the same predetermined distance away from its second end. The elongated loops 278, 280 may be composed of wire, plastic or an elastic material. The interconnect 262 also includes a third hole 274 defined proximal to its second end, and a fourth hole 276, next to the hole 274, also defined proximal to its second end, the holes 274, 276 being positioned and sized such that when the second end of the interconnect 262 is threaded through the rigid loop 258 from bottom to top and then folded upon itself, the holes 274, 276 are aligned with the respective elongated loops 280, 278 so that the elongated loops 280, 278 pass through the respective holes 274, 276 to thereby at least temporarily connect the first end of the interconnect 262 to the rigid loop 254. The holes 274, 276 may optionally be reinforced with rings (for example made from metal or plastic) as shown in FIGS. 3A–3B.

A first enclosed channel 286 is positioned on the connection member 290 and oriented toward the elongated loops 270, 272, and a second enclosed channel 288 is also positioned on the connection member 290 and oriented toward the elongated loops 278, 280. The channels 286, 288 may be composed of a material such as metal, cloth, or plastic and may be independent of one another or connected to form a dual channel 284. A third enclosed channel 292, composed of a flexible material, is preferably centrally disposed along a substantial portion of the length of the connection member 290 between the channels 286, 288 and the distal end of the connection member 290.

Quickly releasable connection of the cuff modules 252, 256 to the interconnect 262 is accomplished by a flexible thin connection line 282 having a first end and a second end, the connection line 282 being sized and configured to fit though the respective elongated loops 270, 272, 278, and 280, once the elongated loops 270, 272, 278, and 280 are passed through the respective holes 266, 268, 276, and 274. The connection line 282 may be any strong thin material such as wire or resilient plastic. Optionally, the connection line 282 may be coated with a resilient material to facilitate passage through the elongated loops 270, 272, 278, and 280. A release tab 294 is attached to the second end of the connection line 282. The release tab 294 preferably includes a releasable connector 296, 298 for releasably securing the release tab 294 to a portion of the connection member 290 between the channel 292 and the releasable connector 300. The releasable connector 296, 298 may be a pair of hook and loop material strips (such as Velcro®) or another set of connection elements such as releasable glue strips, a snap-in button, or the like.

During normal use of the leg restraint system 250, shown in FIG. 3A, the first end of connection line 282 is threaded first through the third channel 292 from the direction of the distal end of the connection member 290, then through the channel 288, through the elongated loops 278, 280, 270, and 272 and inserted into the channel 286. Optionally, upon exiting the channel 292, the first end of connection line 282 may be threaded first through the channel 286, then through the elongated loops 272, 270, 280, and 278 and inserted into the channel 288. The release tab 294 is then releasably connected to the connection member 290 via the releasable connector 296, 298. The connection line 282 serves to connect the cuff modules 252 and 256 to the interconnect 262 by preventing the first and second ends of the interconnect 262 from unfolding from around the respective rigid loops 252 and 258.

In case of an emergency, the cuff modules 252 and 256 may be instantly released from the interconnect 262 as shown in FIG. 3B. First, the release tab 294 is detached from the connection member 290 by disengaging the releasable connector 296, 298, and then pulled sharply to a sufficient distance to cause the second end of the connection line 282 to exit from the elongated loops 270, 272, 278, and 280, to thereby allow instant disconnection of the interconnect 282 from the cuff modules 252, 256 immediately freeing the EDP's legs.

In conclusion, the above-described arm and leg restraint systems of the present invention are easy and intuitive to use and inexpensive to manufacture. The construction of the inventive arm and leg restraint systems makes them easy to deploy in confined areas. Furthermore, the inventive quick release mechanism of the leg restraint system 250 makes it invaluable in case of an emergency.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

I claim:

1. A restraint apparatus for restraining a person for an extended period of time, and for securing the person to at least one seat, comprising:

a first cuff module to be applied to a first wrist of the person, said first cuff module having a first cuff body positioned around the first wrist and a first flexible member connected to said first cuff body terminating in a first releasable connector;

a second cuff module to be applied to a second wrist of the person, said second cuff module having a second cuff body positioned around the second wrist and a second flexible member connected to said second cuff body and terminating in a second releasable connector; and first releasable attachment means for releasably securing said first and said second releasable connectors to the at least one seat, such that the person is thereby restrained and secured to the seat.

2. The restraint apparatus of claim 1, wherein said first releasable attachment means comprises:

a third releasable connector attached to a first area of the at least one seat and configured to releasably connect to said first releasable connector; and a fourth releasable connector attached to a second area of the at least one seat and configured to releasably connect to said second releasable connector.

3. The restraint apparatus of claim 2, wherein said first and said second releasable connectors are one of a male seat-belt type connector or a female seat-belt type connector, and wherein said third and said fourth releasable connectors are the other of said male seat-belt type connector or said female seat-belt type connector.

4. The restraint apparatus of claim 1, wherein said first releasable attachment means comprises:

a first interconnect having a first flexible body of a first length, a first end and an second end and having a fifth releasable connector attached to said first end and configured to releasably connect to said first releasable connector; and a sixth releasable connector attached to said second end and configured to releasably connect to said second releasable connector, and wherein said first interconnect is positioned behind a seat of the at least one seat on which the person is disposed, to thereby secure the person's wrists to the seat once said first and second releasable connectors are releasably connected to said respective fifth and sixth releasable connectors.

5. The restraint apparatus of claim 4, wherein said first and said second releasable connectors are one of a male seat-belt type connector or a female seat-belt type connector, and wherein said fifth and said sixth releasable connectors are the other of said male seat-belt type connector or said female seat-belt type connector.

6. The restraint apparatus of claim 4, wherein said first interconnect further comprises a first tensioning device that controls said first length of said first interconnect, such that when said interconnect is placed behind the seat and said first and said second releasable connectors are releasably connected to said respective fifth and sixth releasable connectors, said first tensioning device is engaged to further secure the person's first and second wrists to the seat.

7. The restraint apparatus of claim 1, further comprising:

a second interconnect comprising first releasable connection means for connecting to said first and said second cuff modules, wherein said second interconnect is sized and configured to wrap around the person's midsection such that said first and said second cuff modules are secured to respective sides of the person's midsection.

8. The restraint apparatus of claim 1, further comprising:

a third cuff module to be applied to a first ankle of the person;

a fourth cuff module to be applied to a second ankle of the person;

a third cuff interconnect having a second flat flexible elongated body of a second length, a top surface, a third end and a fourth end;

an elongated flexible connection element of a third length having a fifth end attached to a central portion of said second body such that said connection element extends perpendicularly thereto, and a sixth end terminating in a seventh releasable connector;

connection means for connecting said third end to said third cuff module, and for connecting said fourth end to said fourth cuff module; and second releasable attachment means for releasably securing said seventh releasable connector to a particular seat of the at least one seat, wherein when said third and fourth cuff modules are applied to the respective first and second ankles and said second releasable attachment means is engaged, the person's legs are thereby secured and immobilized.

9. The restraint apparatus of claim 8, wherein said second releasable attachment means comprises:

an eighth releasable connector, attached to a third area of the particular seat, configured to releasably connect to said seventh releasable connector.

10. The restraint apparatus of claim 8, wherein the particular seat is one of: a seat in front of the seat in which the person is restrained, or a seat behind the seat in which the person is restrained.

11. The restraint apparatus of claim 9, wherein said seventh releasable connector is one of a male seat-belt type connector or a female seat-belt type connector, and wherein said eight releasable connector is the other of said male seat-belt type connector or said female seat-belt type connector.

12. The restraint apparatus of claim 8, further comprising a second tensioning device positioned on said connection element for changing said second length, such that when said second attachment means is engaged, said second tensioning device is selectively engaged to reduce said second length to better secure and immobilize the person's legs.

13. The restraint apparatus of claim 8, wherein said connection means comprises a third releasable attachment means for releasably connecting said third cuff interconnect to said third and said fourth cuff modules.

14. The restraint apparatus of claim 13, wherein said third cuff module comprises a first rigid loop disposed perpendicular thereto, wherein said fourth cuff module comprises a second rigid loop disposed perpendicular thereto, said first and second rigid loops being sized and configured to accept said third and fourth ends, respectively, and wherein said third releasable attachment means comprises:

a first elongated loop positioned on said top surface at a predetermined distance from said third end;

a second elongated loop positioned next to said first elongated loop on said top surface at said predetermined distance from said third end;

a first hole defined proximal to said third end, and a second hole, next to said first hole, defined proximal to said third end, said first and second holes being positioned and sized such that when said third end is threaded through said first rigid loop in an upward direction, and then folded upon itself, said first and second holes are aligned with said first and second elongated loops, respectively, so that said first and second elongated loops pass through respective said first and second holes to thereby at least temporarily connect said third end of said second body to said first rigid loop;

a third elongated loop positioned on said top surface at said predetermined distance from said fourth end;

a fourth elongated loop positioned next to said third elongated loop on said top surface at said predetermined distance from said fourth end;

a third hole defined proximal to said fourth end, and a fourth hole, next to said third hole, defined proximal to said fourth end, said third and fourth holes being positioned and sized such that when said second end is threaded through said second rigid loop in an upward direction, and then folded upon itself, said third and fourth holes are aligned with said third and fourth elongated loops, respectively, so that said third and fourth elongated loops pass through said third and fourth holes, respectively, to thereby at least temporarily connect said fourth end of said second body to said second rigid loop;

a first enclosed channel positioned on said fifth end of said connection element, said first channel being oriented toward said first and second elongated loops;

a second enclosed channel positioned on said fifth end of said connection element, said second channel being oriented toward said third and fourth elongated loops;

an elongated third enclosed channel positioned along a substantial length of said connection element and having a proximal end oriented toward said first and said second channels, and a distal end oriented toward said seventh connector;

a flexible thin elongated connection line, sized and configured to readily pass through said first, second and third channels and through said first, second, third and fourth elongated loops when said first, second, third and fourth elongated loops are passed though said respective first, second, third, and fourth respective holes; said connection line having a seventh end and an eight end; and a tab connected to said eighth end of said connection line, wherein when said first, second, third and fourth elongated loops are passed though said respective first, second, third, and fourth respective holes and said seventh end of said connection line is threaded through said first, second and third channels and then through said first, second, third and fourth elongated loops, said third and fourth cuff modules are securely connected to said third cuff interconnect, and wherein to quickly disconnect said third and fourth cuff modules from said third cuff interconnect, said tab is pulled until said seventh end of said connection line is threaded back out from said first, second, third and fourth elongated loops to enable instant removal of said first, second, third and fourth holes from said first, second, third and fourth elongated loops, thereby quickly releasing said third and fourth cuff modules from said third cuff interconnect.

15. The restraint apparatus of claim 14, further comprising a fourth releasable attachment means for releasably connecting said tab to said connection element to prevent said tab from moving, such that said tab cannot be pulled without first disengaging said fourth releasable attachment means.

16. The restraint apparatus of claim 15, wherein said fourth releasable attachment means comprises:

a first attachment element, positioned on said tab, comprising one of hook or loop attachment material, and a second attachment element, positioned on said connection element between said distal end of said third channel and said seventh connector, comprising the other of hook or loop attachment material, such that when said fourth releasable attachment means is engaged, said first attachment element is releasably connected to said second attachment element.

17. The restraint apparatus of claim 14, further comprising: a first ring positioned and configured to reinforce said first hole, a second ring positioned and configured to reinforce said second hole, a third ring positioned and configured to reinforce said third hole, and a fourth ring positioned and configured to reinforce said fourth hole.

18. The restraint apparatus of claim 14, wherein said connection line is selected from a group consisting of: a wire, a flexible plastic member, and a wire coated with a resilient material.

19. A method for restraining a person for an extended period of time, and for securing the person to at least one seat, comprising the steps of:

(a) applying a first cuff module to a first wrist of the person, said first cuff module having a first cuff body and a first flexible member connected to said first cuff body terminating in a first releasable connector;

(b) applying a second cuff module to a second wrist of the person, said second cuff module having a second cuff body and a second flexible member connected to said second cuff body and terminating in a second releasable connector; and (c) releasably securing said first and said second releasable connectors to the at least one seat, such that the person is thereby restrained and secured to the seat.

20. The method of claim 19, wherein said step (c) comprises the steps of:

(d) releasably connecting said first releasable connector to a third releasable connector attached to a first area of the at least one seat; and (e) releasably connecting said second releasable connector to a fourth releasable connector attached to a second area of the at least one seat.

21. The method of claim 19, wherein said step (c) comprises the steps of:

(f) providing a first interconnect having a first flexible body of a first length, a first end and an second end and having a fifth releasable connector attached to said first end and configured to releasably connect to said first releasable connector; and a sixth releasable connector attached to said second end and configured to releasably connect to said second releasable connector, (g) positioning said first interconnect behind a seat of the at least one seat on which the person is disposed; and (h) releasably connecting said first and second releasable connectors to said respective fifth and sixth releasable connectors to thereby secure the person's wrists to the seat.

22. The method of claim 21, further comprising the step of:

(i) after said step (h), engaging a first tensioning device, positioned on said first interconnect, to reduce said first length of said first interconnect to further secure the person's first and second wrists to the seat.

23. The method of claim 19, further comprising the step of:

(j) providing a second interconnect comprising a first releasable connector that connects to said first and said second cuff modules, sized and configured to wrap around the person's midsection; and (k) wrapping said second interconnect around the person's midsection such that said first and said second cuff modules are secured to respective sides of the person's midsection.

24. The method of claim 19, further comprising the steps of:

(l) applying a third cuff module to a first ankle of the person;

(m) applying a fourth cuff module to a second ankle of the person;

(n) providing a third cuff interconnect having a second flat flexible elongated body of a second length, a top surface, a third end and a fourth end;

(o) connecting said third end to said third cuff module and said fourth end to said fourth cuff module;

(p) providing an elongated flexible connection element of a third length having a fifth end, and a sixth end terminating in a seventh releasable connector;

(q) attaching said connection element to a central portion of said second body such that said connection element extends perpendicularly thereto; and (r) releasably securing said seventh releasable connector to one of the at least one seat to thereby secure and immobilize the person's legs.

25. The method of claim 24, further comprising the step of:

(s) after said step (r), engaging a second tensioning device, positioned on said first connection element, that changes said second length, to reduce said second length to better secure and immobilize the person's legs.

26. The method of claim 24, wherein said step (o) comprises the step of:

(t) releasably connecting said third cuff interconnect to said third and said fourth cuff modules.

27. The method of claim 26, wherein said third cuff module further comprises a first rigid loop disposed perpendicular thereto, wherein said fourth cuff module further comprises a second rigid loop disposed perpendicular thereto, said first and second rigid loops being sized and configured to accept said third and fourth ends, respectively, wherein said third cuff interconnect further comprises: (1) a first elongated loop positioned on said top surface at a predetermined distance from said third end, (2) a second elongated loop positioned next to said first elongated loop on said top surface at said predetermined distance from said third end, (3) a first hole defined proximal to said third end, (4) a second hole, next to said first hole, defined proximal to said third end, said first and second holes being positioned and sized such that when said third end is threaded through said first rigid loop in an upward direction, and then folded upon itself, said first and second holes are aligned with said first and second elongated loops, respectively, so that said first and second elongated loops pass through respective said first and second holes, (5) a third elongated loop positioned on said top surface at said first predetermined distance from said fourth end, (6) a fourth elongated loop positioned next to said third elongated loop on said top surface at said predetermined distance from said fourth end, (7) a third hole defined proximal to said fourth end, (8) a fourth hole, next to said third hole, defined proximal to said fourth end, said third and fourth holes being positioned and sized such that when said second end is threaded through said second rigid loop in an upward direction, and then folded upon itself, said third and fourth holes are aligned with said third and fourth elongated loops, respectively, so that said third and fourth elongated loops pass through said third and fourth holes, respectively; wherein said fifth end of said connection element further comprises a first enclosed channel positioned on said fifth end of said connection element, said first channel being oriented toward said first and second elongated loops and a second enclosed channel positioned on said fifth end of said connection element, said second channel being oriented toward said third and fourth elongated loops; wherein said connection element further comprises an elongated third enclosed channel, positioned along a substantial length thereof, and having a proximal end oriented toward said first and said second channels, and a distal end oriented toward said seventh connector; and wherein said step (t) comprises the steps of:

(u) providing a flexible thin elongated connection line, sized and configured to readily pass through said first, second and third channels and through said first, second, third and fourth elongated loops when said first, second, third and fourth elongated loops are passed though said respective first, second, third, and fourth respective holes; said connection line having a seventh end and an eight end, and a tab connected to said eighth end;

(v) passing said first, second, third and fourth elongated loops through said respective first, second, third, and fourth respective holes; and (w) threading said seventh end of said connection line through said first, second and third channels and through said first, second, third and fourth elongated loops to thereby securely connect said third and fourth cuff modules are to said third cuff interconnect.

28. The method of claim 27, further comprising the step of:

(x) disconnecting said third and fourth cuff modules from said third cuff interconnect, by pulling said tab until said seventh end of said connection line is threaded back out from said first, second, third and fourth elongated loops to enable removal of said first, second, third and fourth holes from said first, second, third and fourth elongated loops, thereby quickly releasing said third and fourth cuff modules from said third cuff interconnect.

29. The method of claim 27, further comprising the step of:

(y) releasably connecting said tab to said connection element to prevent said tab from moving, such that said step (x) cannot be performed until said step (y) is performed.

* * * * *